United States Patent [19]

Dieckelmann et al.

[11] Patent Number: 4,584,390
[45] Date of Patent: Apr. 22, 1986

[54] CONTINUOUS PROCESS FOR THE CATALYTIC EPOXIDATION OF OLEFINIC DOUBLE BONDS WITH HYDROGEN PEROXIDE AND FORMIC ACID

[75] Inventors: Gerhard Dieckelmann, Hilden; Klemens Eckwert, Duesseldorf; Lutz Jeromin; Eberhard Peukert, both of Hilden; Udo Steinberner, Erkrath, all of Fed. Rep. of Germany

[73] Assignee: Henkel Kommanditgesellschaft auf Aktien, Duesseldorf, Fed. Rep. of Germany

[21] Appl. No.: 615,446

[22] Filed: May 30, 1984

[30] Foreign Application Priority Data

Jun. 3, 1983 [DE] Fed. Rep. of Germany ....... 3320219

[51] Int. Cl.$^4$ ........................................... C07D 301/16
[52] U.S. Cl. ..................................... 549/526; 549/527
[58] Field of Search .............................. 549/526, 527

[56] References Cited

PUBLICATIONS

Ullman's Encyclopadie der Technischen Chemie, Verlag Chemie Weinheim (1975), vol. 10, p. 574.

Primary Examiner—Norma S. Milestone
Attorney, Agent, or Firm—Ernest G. Szoke; Henry E. Millson, Jr.; Mark A. Greenfield

[57] ABSTRACT

In a multistage process for the continuous epoxidation of double bonds of terminal and non-terminal olefins containing more than 12 carbon atoms, unsaturated higher fatty acids and their lower alkanol and lower alkanediol esters and also unsaturated fatty alcohols containing from 8 to 18, preferably 18, carbon atoms and triglycerides of higher fatty acids including unsaturated fatty acids, preferably soyabean oil, using performic acid formed in situ from hydrogen peroxide and formic acid, the reactants, olefin and hydrogen peroxide/formic acid, are passed at ambient pressure in cross-counter flow through an at least three-stage reaction cascade. The olefinic phase is introduced into the first reaction stage, the hydrogen peroxide and the formic acid are introduced in separate streams into the penultimate reaction stage and the olefin phase and the hydrogen peroxide/formic acid phase (acid water phase) are separated from one another in a phase separator after each reaction stage. The olefinic phase passes successively through reaction stages I to n while the acid water, after reaction stage (n−1), passes through reaction stages (n−2) to 2 in counter flow to the olefin phase and then through stages n and 1, the reaction temperature being maintained in the range from 50° to 80° C. in the reactors and in the range from 15° to 60° C. in the phase separators.

14 Claims, 8 Drawing Figures

CONTINUOUS PROCESS FOR THE CATALYTIC EPOXIDATION OF OLEFINIC DOUBLE BONDS WITH HYDROGEN PEROXIDE AND FORMIC ACID

BACKGROUND OF THE INVENTION

This invention relates to a multistage process for the continuous epoxidation of double bonds of terminal and non-terminal olefins containing more than 12 carbon atoms, unsaturated higher fatty acids and their esters, especially lower alkanol esters, and also unsaturated hydrocarbon alcohols containing from 8 to 18, preferably 18, carbon atoms in the alcohol radical and triglycerides of unsaturated higher fatty acids, preferably soyabean oil, with hydrogen peroxide and formic acid in the presence of a catalyst.

The epoxidation of unsaturated fatty acid derivatives, primarily soyabean oil, is carried out on an industrial scale, giving plasticizers which are compatible with polyvinyl chloride (PVC) and which also act as stabilizers, primarily against heat degradation (Ullmann's Encyclopadie der Technischen Chemie, Verlag Chemie Weinheim (1975), Vol. 10, 574). According to the Federal Republic of Germany Office of Health and the U.S. Food and Drug Administration, epoxidized soyabean oil is also accepted as an additive for plastics which come into contact with foods.

At present, the preferred epoxidizing agent is performic acid which may be formed in situ from formic acid and hydrogen peroxide. The reaction takes place in a heterogeneous mixture of peracid-containing aqueous phase and an oil phase at a slightly elevated temperature (50°–80° C.).

It is known that the operation of chemical processes in a continuous cascade of stirrer-equipped vessels gives poorer yields and conversions on account of the residence time spectrum than the batch process carried out in a stirrer-equipped vessel, because a corresponding conversion can only be obtained after a longer average residence time or by large excesses of one or more reactants. In the epoxidation of fatty acid derivatives, the residence time cannot be increased as required without affecting the epoxide yield, because undesirable epoxide derivatives are formed during epoxidation through ring-opening reactions which are largely initiated by the formic acid used. For the same reason, the concentration of formic acid also cannot be increased beyond a certain value.

In addition, it is necessary for reasons of industrial safety to keep the concentration of performic acid as low as possible because this strongly oxidizing acid can react explosively on heating or on contact with metals, such as for example iron or copper, or on contact with strongly reducing compounds.

The only remaining possibility of obtaining high yields in the continuous process carried out in a cascade of stirrer-equipped vessels is to increase the excess of $H_2O_2$ by comparison with the batch process.

The quality of the olefinic starting material and of the corresponding epoxides is essentially determined by two characteristics, namely the iodine number (IN) and the epoxide value (EPO). Whereas the iodine number is a measure of the number of unsaturated double bonds, the epoxide value is an indication of the percentage content (% by weight) of epoxide oxygen. Accordingly, it is a measure of the epoxide yield. The quality of the epoxide is better, the higher the epoxide value and the lower the iodine number.

For example, a soyabean oil epoxide of very high quality is characterized by an IN of $\leq 2.5$ and an EPO of $\geq 6.5$, while a soyabean oil epoxide of high quality is characterized by an IN of $\leq 5.0$ and an EPO of $\geq 6.3$. Soyabean oil epoxide having an iodine number of more than 5.0 or an epoxide value of less than 6.3 is regarded as being of poor quality from the point of view of practical application. Accordingly the object of any epoxidation process must be to produce an epoxide which has both a low iodine number and also a high epoxide value.

Whereas a low iodine number which corresponds to a high conversion can always be obtained by a correspondingly long residence time, even with a small excess of hydrogen peroxide, there is an optimal residence time for the maximum epoxide yield. If this is exceeded, the epoxide value falls again.

In both the cascade process and also in the batch epoxidation process, the density of the heavier aqueous phase (also referred hereinafter as "acid water"), decreases as the reaction progresses while the density of the oily phase increases. The difference in density between the phases becomes very small, making the phases difficult to separate by gravity separation. In addition, the heat generated during the epoxidation reaction produces convection currents in the separator on account of temperature gradients. These convection currents are intensified by ascending gas bubbles which are formed during the decomposition of the aqueous phase.

OBJECTS OF THE INVENTION

An object of the present invention is the development of a continuous process of epoxidation of unsaturated oily compounds by a "cross-counter flow process" whereby effective phase separation by gravity separation is obtained. In each reaction stage, concentrations are established which guarantee a difference in density between the aqueous phase and the oily phase which is sufficient for phase separation. Separation is further promoted by inert packings such as of glass or ceramics.

Another object of the present invention is the development of a multistage process for the continuous epoxidation of double bonds of an unsaturated oily compound selected from the group consisting of terminal and non-terminal olefins having more than 12 carbon atoms, unsaturated higher fatty acids and their esters with lower alkanols and lower alkanediols, unsaturated aliphatic hydrocarbon alcohols having from 8 to 18 carbon atoms and triglycerides of higher fatty acids including unsaturated higher fatty acids using performic acid formed in situ from hydrogen peroxide and formic acid in an aqueous media consisting essentially of passing the reactants, the unsaturated oily compound and the hydrogen peroxide/formic acid aqueous phase under ambient pressure in cross-counter flow through an at least three-stage reaction cascade from stage 1 to stage n, of which the individual stages each consist of a stirrer-equipped reaction vessel and a phase separator, the oily phase being introduced into the first reaction stage, the concentrated hydrogen peroxide solution being introduced into the penultimate reaction stage and the concentrated formic acid solution being introduced as a separate steam into one or more of the stages $n-1$, $n-2$ or $n-3$ to 2, the oily phase and the hydrogen peroxide/formic acid aqueous phase or acid water phase being separated from one another in a phase separator in each reaction stage after issuing from the reactor and the olefinic phase successively passing through reaction stages 1 to n, while the acid water phase, after reaction stage (n−1), passes through the reaction stages (n−2) to 2 in counterflow to the olefin phase and then through stages n and 1, while the reaction temperature is maintained between 50° and 80° C. in the reactors and between 15° and 60° C. in the phase separators, and continuously recovering an epoxidized oily compound from reaction stage n and an acid water phase from reaction stage 1. become more apparent as the description thereof proceeds.

DESCRIPTION OF THE INVENTION

Accordingly, the present invention relates to a multistage process for the continuous epoxidation of double bonds of terminal and non-terminal olefins containing more than 12 carbon atoms, unsaturated higher fatty acids and their esters and also unsaturated alcohols containing from 8 to 18, preferably 18, carbon atoms and triglycerides, preferably soyabean oil, using performic acid formed in situ from hydrogen peroxide and formic acid, characterized in that the reactants, olefin and hydrogen peroxide/formic acid, are passed in cross-counter flow at ambient pressure through an at least three-stage and preferably four-stage reaction cascade, of which the individual stages each consist of a stirrer-equipped reaction vessel and a phase separator, the olefin phase being introduced into the first reaction stage and the hydrogen peroxide and formic acid being introduced in separate streams into the penultimate reaction stage while the olefin phase and the hydrogen peroxide/formic acid phase or acid water phase are separated from one another in a phase separator in each reaction stage after issuing from the reactor, the olefin phase successively passing through reaction stage 1 to n while the acid water, after the reaction stage (n−1), passes through the reaction stages in the order (n−2) to 2 in counter flow to the olefin phase and then through the stages n and 1, the reaction temperature being in the range from 50° to 80° C. and preferably in the range from 60° to 70° C. in the reactors and in the range from 15° to 60° C. and preferably in the range from 40° to 50° C. in the phase separators.

More particularly, the present invention relates to a multistage process for the continuous epoxidation of double bonds of an unsaturated oily compound selected from the group consisting of terminal and non-terminal olefins having more than 12 carbon atoms, unsaturated higher fatty acids and their esters with lower alkanols and lower alkanediols, unsaturated aliphatic hydrocarbon alcohols having from 8 to 18 carbon atoms and triglycerides of higher fatty acids including unsaturated higher fatty acids using performic acid formed in situ from hydrogen peroxide and formic acid in an aqueous media consisting essentially of passing the reactants, the unsaturated oily compound and the hydrogen peroxide/formic acid aqueous phase under ambient pressure in cross-counter flow through an at least three-stage reaction cascade from stage 1 to stage n, of which the individual stages each consist of a stirrer-equipped reaction vessel and a phase separator, the oily phase being introduced into the first reaction stage, the concentrated hydrogen peroxide solution being introduced into the penultimate reaction stage and the concentrated formic acid solution being introduced as a separate stream into one or more of the stages n−1, n−2 or n−3 to 2, the oily phase and the hydrogen peroxide/formic acid aqueous phase or acid water phase being separated from one another in a phase separator in each reaction stage after issuing from the reactor and the olefinic phase successively passing through reaction stages 1 to n, while the acid water phase, after reaction stage (n−1), passes through the reaction stages (n−2) to 2 in counter flow to the olefin phase and then through stages n and 1, while the reaction temperature is maintained between 50° and 80° C. in the reactors and between 15° and 60° C. in the phase separators, and continuously recovering an epoxidized oily compound from reaction stage n and an acid water phase from reaction stage 1.

If the number n of reaction stages selected is n ≠ 4, the following applies to the passage of the phases containing the reactants: The olefinic oily phase always passes through the number of reaction stages in ascending order from 1 to n. The main point of addition for the reactants hydrogen peroxide and formic acid is in the reactor of stage (n−1). After passing through to reaction stage 2 in counter flow to the olefinic oily phase, the acid water phase is passed through the $n^{th}$ stage to reaction stage 1. The hydrogen peroxide and/or formic acid stream may have to be divided up, depending on the nature of the olefinic oily phase. If so, it is divided up between reactors of stages (n−1) to 2. In that case, an after-reaction vessel following the $n^{th}$ stage is not counted as an independent reaction stage because there is no phase separator which belongs to that unit.

In order to obtain effective phase separation, it is important for the reaction in the phase separator to be stopped immediately and for decomposition of the aqueous phase already separated to be suppressed. For this reason, each separator comprises two built-in, independently operated heat exchangers for cooling the olefinic oily phase and the aqueous phase. The aqueous phase is kept as cold as possible to avoid decomposition losses of hydrogen peroxide and formic acid and not to impair separation of the aqueous phase from the olefinic oily phase through ascending $CO_2$-bubbles which are formed during decomposition of the performic acid. To that end, the aqueous phase is cooled to a temperature of from 15° to 40° C. and preferably to a temperature of 20° C.

Since the difference in density between the olefinic oily phase and the aqueous phase decreases with decreasing temperature, the mixture of homogeneous olefinic oily phase and disperse aqueous phase being injected into the separator must not be excessively cooled in the separator. Accordingly, the temperatures in the olefinic oily phase are between 30° and 60° C. and, hence, up to 30° C. lower than the reactor temperature of the corresponding stage. This also prevents an uncontrolled after-reaction which begins at 50° to 70° C., depending upon the concentration levels.

The hot reaction mixture of homogeneous olefinic oily phase and dispersed aqueous phase issuing from the reactor is introduced into the separator beneath the phase interface but above the bottom of the separator. In view of the difference in density, it rises and passes through the cold aqueous phase, as a result of which it is cooled and the reaction is stopped. In addition, some of the acid water is actually removed from the reaction mixture as it passes through the aqueous phase.

Through the separation of the phases, the crosscounter flow process can be carried out in an apparatus by which it is possible to obtain, in comparison with the batch process, higher epoxide yields for the same excess of $H_2O_2$ or the same epoxide yields for a smaller excess of $H_2O_2$. The reactants are added in such a way that even incomplete separation of the phases due to the solubility of hydrogen peroxide and formic acid in the olefin-containing phase does not lead to losses of acid water.

Figure 1:
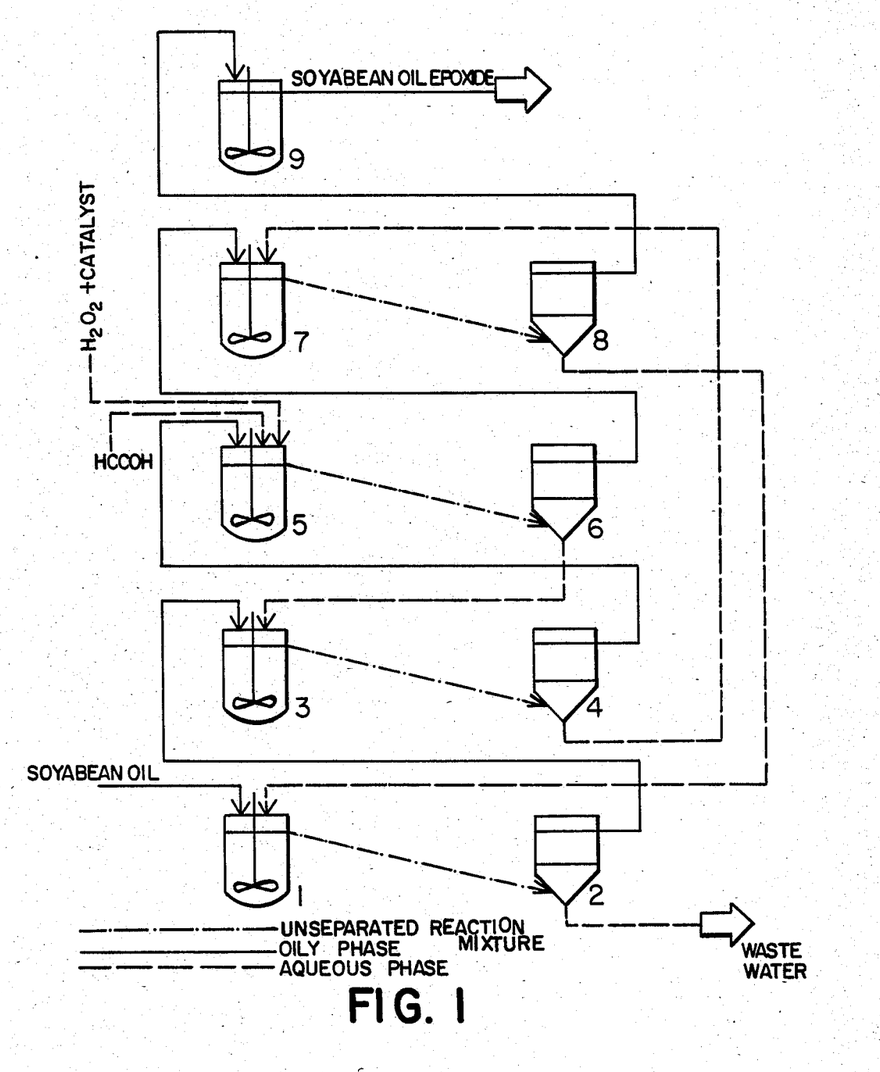
FIG. 1 is a flow chart of one embodiment of process of the invention.

The continuous reaction of compounds containing olefinic double bonds to form the corresponding epoxides is carried out in a multistage apparatus which operates at ambient pressure on the mixer-separator principle and of which the flow chart is shown in FIG. 1.

Each stage comprises a stirrer-equipped vessel as reactor 1,3,5,7 and 9, in which the reaction takes place in the liquid phase. The reaction mixture issuing from the reactor, which consists of partly epoxidized olefin, hydrogen peroxide, formic acid, water and catalyst, is separated in the separator 2, 4, 6 and 8 into an aqueous phase, consisting of hydrogen peroxide, formic acid, water and catalyst, and an olefinic phase consisting of an olefinic oily phase epoxidized in accordance with the particular reaction stage and dissolved or dispersed fractions of the aqueous phase. The olefinic oily phase and the aqueous phase are subsequently delivered to the reactors of different stages. The solid line shows the passage of the olefinic oily phase, the dashed line shows the passage of the aqueous phase, and the dotted line shows the passage of the unseparated reaction mixture.

The reactant containing olefinic double bonds is dded in the reactor 1. It then passes through the separators and reactors in ascending number order from 2 to 9. 70% hydrogen peroxide solution together with catalyst and 85% formic acid solution are introduced into the reactor 5. The aqueous phase passes through the reactors and separators in the order 5 - 6 - 3 - 4 - 7 - 8 - 1 - 2. In the reactor 7, the highly concentrated acid water dissolved in the olefin phase in the separator 6 and carried over is washed out with the low-concentration aqueous phase from the separator 4 and subsequently delivered to the reactor 1 after separation from the olefin-containing phase in the separator 8. The olefinic phase from the separator 8 passes together with the acid water which has not been separated into the afterreaction vessel 9 where the entrained hydrogen peroxide is further degraded.

The temperatures in the reactors are kept constant by indirect cooling and amount to between 50° and 80° C. and preferably to 70° C. in the reactors 1, 3, 5 and 7; in the afterreaction vessel 9, the temperature amounts to between 40° and 60° C. and preferably to 50° C. The average residence time per reactor amounts to between 1.5 and 2 hours in reactors 1, 3, 5 and 7 and to between 3 and 8 hours in the afterreaction vessel 9.

The separators have the same useful volumes as the reactors of the corresponding stages. The residence time of the aqueous phase should be as short as is structurally possible to avoid decomposition losses and to enable unstable variations in operation, such as can occur for example during startup of the apparatus, to be quickly corrected.

The position of the separating layer between the olefin/epoxide phase and the acid water phase in the separators is adjusted in such a way that the ratio by volume between the acid water phase and the oily olefin/epoxide phase in the separators is smaller than or at most equal to that of the input streams, so that the average residence time of the acid water phase in the separators is shorter than or at most equal to that of the oily olefix/epoxide phase.

Because the separators are cooled, the temperatures of the streams delivered to the reactors are lower than the corresponding reaction temperatures. The reactors are partly cooled by the streams flowing in, thereby relieving the cooling systems of the reactors.

In the cross-counter flow process, there is no need at all to use a catalyst. However, the catalysts known for in situ epoxidation reactions, such as sulfuric acid or phosphoric acid, may be used in order to shorten the residence time. It is particularly advantageous to use hydroxy ethane-1,2-diphosphonic acid (HEDP) because this acid has not only a catalytic effect, but also a stabilizing effect on $H_2O_2$, so that only small quantities of hydrogen peroxide are lost through decomposition.

The hydrogen peroxide solution employed is as concentrated as possible, and ordinarily has a concentration of from 50% to 90%, preferably from 80% to 90%. The formic acid employed ordinarily has a concentration of from 70% to 100%, preferably from 85% to 100%. For each olefinic double bond epoxidized, one equivalent of $H_2O$ is liberated.

The invention is illustrated by the following Examples.

EXAMPLE 1

40 kg/h of soyabean oil having an iodine number of 130, which corresponds to a theoretically attainable epoxide value (epoxide oxygen content) of 7.57, were continuously epoxidized in cross-counter flow in a four-stage mixer-settler. The reactors and separators each had a useful volume of 100 L.

Figure 2:
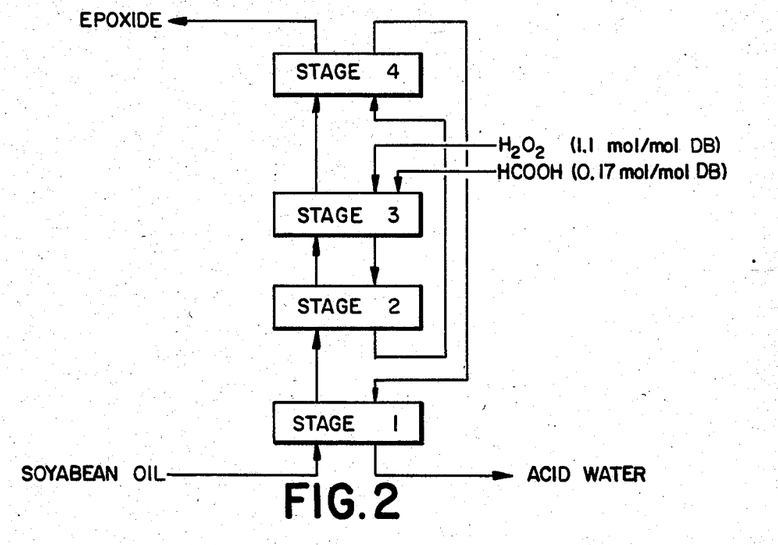
FIG. 2 is a flow chart of the embodiment of Example 1.

The paths followed by the various streams are shown diagrammatically in FIG. 2. 10.9 kg/h (1.1 mol/mol of double bond (DB)) of 70% hydrogen peroxide and 1.88 kg/h (0.17 mol/mol of DB) of 85% formic acid were introduced into the third stage. To stabilize the aqueous phase, 0.1 kg/h of hydroxyethane-1,2-diphosphonic acid (HEDP) was added to the stream of $H_2O_2$. In each separator, the oil phase and the aqueous phase were separately cooled, so that the temperature of the oil phase amounted to approximately 45° C. and the temperature of the aqueous phase to 20° C. The reaction was carried out at 70° C. in all the reactors.

The soyabean oil epoxide having an epoxide oxygen content of 6.47% and an iodine number of 5.6 was obtained. The discharged acid water leaving the unit had a hydrogen peroxide concentration of 6.2% by weight.

EXAMPLE 2

Figure 3:
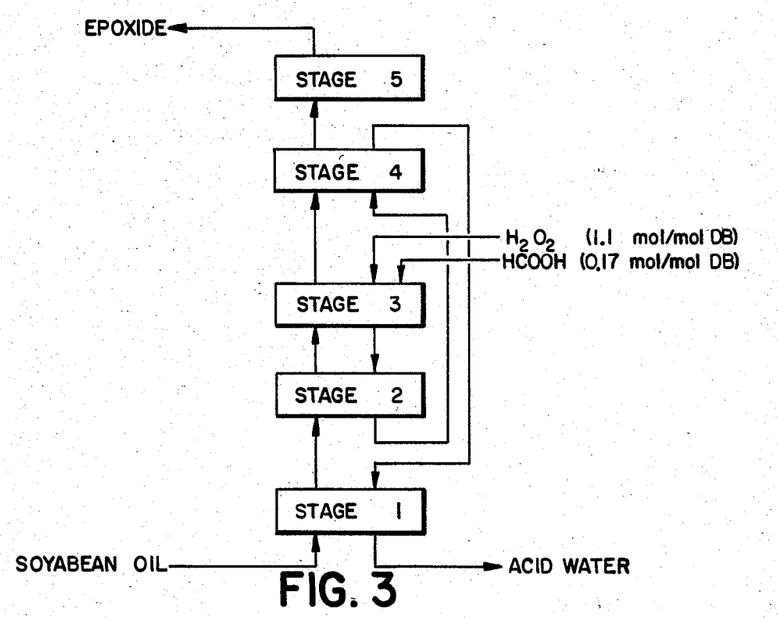
FIG. 3 is a flow chart of the embodiment of Example 2.

The procedure was the same as in Example 1 using an additional afterreaction vessel (useful volume 300 L), in which the double bonds still present were further reacted with constituents of the aqueous phase dissolved and dispersed in the olefin phase at a temperature of 50° C. (FIG. 3). As a result, the epoxide value rose to 6.55% and the iodine number fell to 2.8.

EXAMPLE 3

Figure 4:
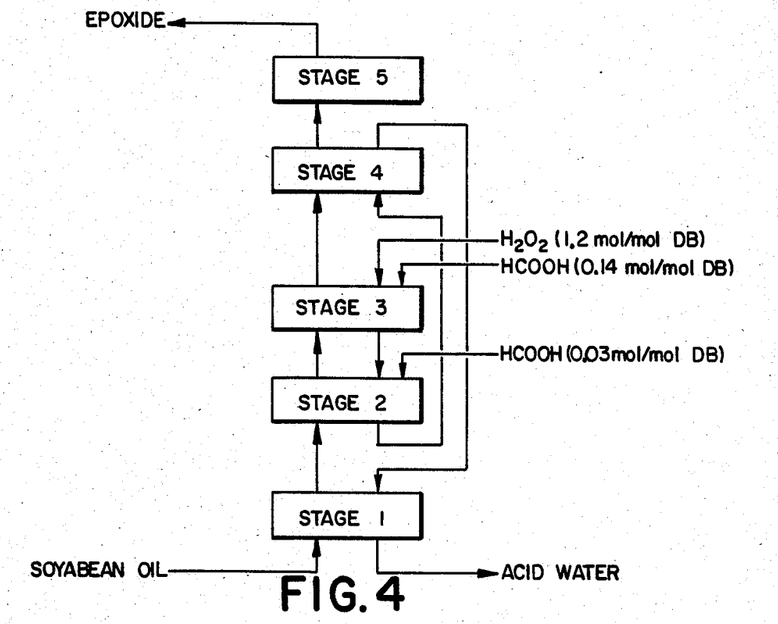
FIG. 4 is a flow chart of the embodiment of Example 3.

The procedure was the same as in Example 2, except the $H_2O_2$-input was increased to 11.9 kg/h (1.2 mol/mol of DB) and the formic acid was divided up between the second and third stages (see FIG. 4), so that 0.03 mol/mol of DB were introduced into the second stage and 0.14 mol/mol of DB into the third stage. The reactor temperature of the fourth stage was reduced to 60° C. All other temperatures corresponded to those of Example 2. The epoxide obtained had an epoxide value of 6.62% and an iodine number of 2.2.

EXAMPLE 4
(Comparison Example)

The procedure was the same as in Example 1, except that the separators were not cooled, so that the reaction mixture afterreacted in the separators at around 60° C., producing a significant deterioration in phase separation. An epoxide value of only 5.88% and an iodine number reduction to only 17.5 were obtained.

EXAMPLE 5
(Comparison Example)

Figure 5:
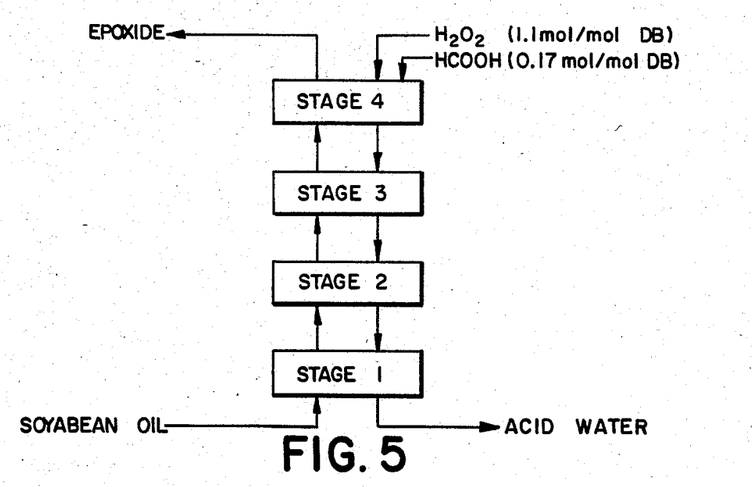
FIG. 5 is a flow chart of the prior art comparison Example 5.

The product streams were passed through the apparatus in counter flow as shown in FIG. 5. The quantities used and also the temperatures of the reactors and separators corresponded to those of Example 1. Although the hydrogen peroxide of the aqueous phase was degraded to 5.0% by weight, the soyabean oil epoxide had an epoxide value of only 6.03% and an iodine number of 8.2 because some of the highly concentrated acid water was removed by the oil phase in the fourth stage as a result of incomplete phase separation.

EXAMPLE 6
(Comparison Example)

Figure 6:
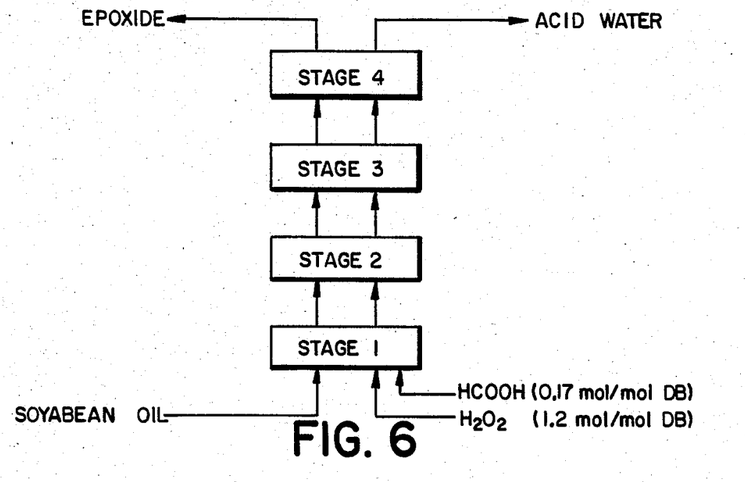
FIG. 6 is a flow chart of the prior art comparison Example 6.

The soyabean oil used was epoxidized in a fourstage parallel-flow cascade with no separator, see FIG. 6. The quantities used amounted respectively to 40 kg/h of soyabean oil, 11.9 kg/h (1.2 mol/mol of DB) of 70% hydrogen peroxide, 1.88 kg/h (0.17 mol/mol of DB) of 85% formic acid and 0.1 kg/h of hydroxyethane1,2-diphosphonic acid. All the reaction components were introduced into the first stage and then passed through stages 2, 3 and 4. The reactors were identical with those of Example 1. The reaction temperature was 70° C. in all the reactors.

Under these reaction conditions, a soyabean oil epoxide was recovered with an epoxide value of 6.37% and an iodine number of 4.7. The hydrogen peroxide used was degraded to 14.8% by weight (based on the aqueous phase from the fourth stage).

EXAMPLE 7

Figure 7:
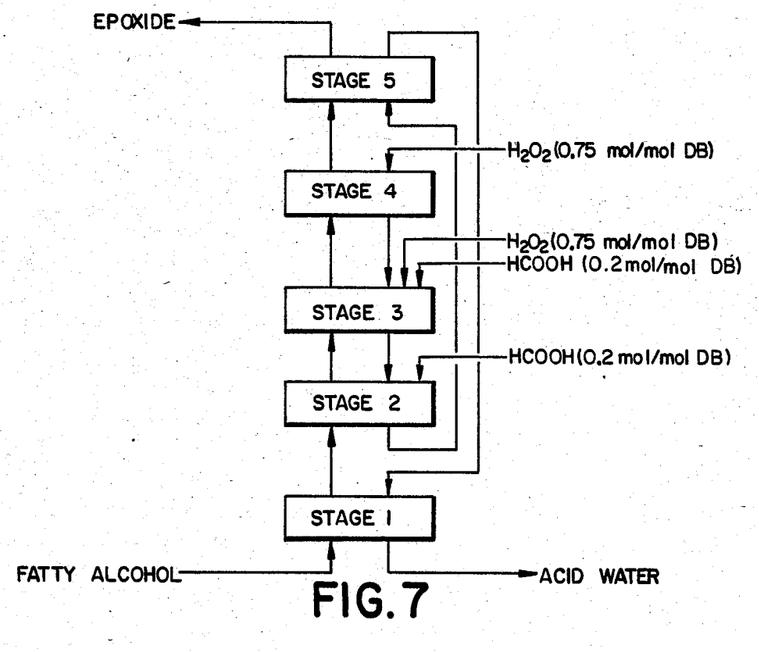
FIG. 7 is a flow chart of the embodiment of Example 7.

Ocenol ® (an unsaturated $C_{16-18}$-fatty alcohol having an iodine number of 88.3) was epoxidized in a five-stage mixer-settler of the type illustrated in FIG. 7. The reactors and separators each had a useful volume of 100 liters. The quantities used amounted respectively to 60 kg/h of the unsaturated fatty alcohol, 15.2 kg/h (1.5 mol/mol of DB) of 70% hydrogen peroxide, 4.52 kg/h (0.4 mol/mol of DB) of 85% formic acid and 0.14 kg/h of hydroxyethane-1,2-diphosphonic acid which was added to the hydrogen peroxide. On account of the solubility of hydrogen peroxide and formic acid in the alcohol phase, the input of hydrogen peroxide was divided up between the third and fourth stages and the input of formic acid between the second and third stages. The reaction was carried out at 70° C. in stages 1 to 4 and at 60° C. in stage 5. In the separators, the olefin phase was cooled to 50° C. and the aqueous phase to 20° C.

The epoxide produced in this way had an epoxide value of 4.1% and a residual iodine number of 2.1, which corresponded to a yield of 77.8% and to a conversion of 97.6%.

EXAMPLE 8

Figure 8:
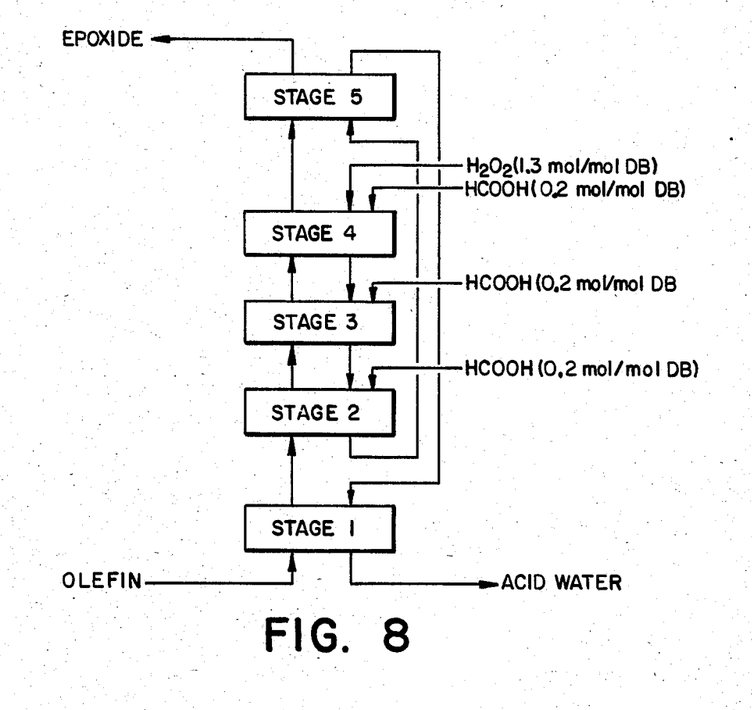
FIG. 8 is a flow chart of the embodiment of Example 8.

The α-olefin, 1-dodecene, was continuously epoxidized in the five-stage mixer-settler of the type shown in FIG. 8. Starting from an iodine number of 148.2, it would be possible to obtain a theoretical epoxide value of 8.54%.

12 kg/h of olefin were introduced into the first stage and 4.42 kg/h (1.3 mol/mol of DB) of 70% hydrogen peroxide together with 0.05 kg/h of HEDP into the fourth stage. The 85% formic acid was divided in equal parts between stages 2, 3 and 4 to minimize the decomposition losses. In all, 2.275 kg/h (0.6 mol/mol of DB) of formic acid solution were used.

The reactors and separators each had a useful volume of 100 L. The temperature in all the reactors was 60° C. In the separators, the temperature of the olefin phase was kept at 40° C. and the temperature of the acid water phase at 20° C. Under these reaction conditions, an epoxide value of 4.58% and an iodine number of 47.7 were obtained. This corresponded to a yield of 53.6% for a conversion of 68.2%. The discharge acid water leaving the unit had an $H_2O_2$-concentration of 6.7%.

The preceding specific embodiments are illustrative of the practice of the invention. It is to be understood however, that other expedients known to those skilled in the art or disclosed herein may be employed without departing from the spirit of the invention or the scope of the appended claims.

We claim:

1. A multistage process for the continuous expoxidation of double bonds of an unsaturated oily compound selected from the group consisting of terminal and non-terminal olefins having more than 12 carbon atoms, unsaturated higher fatty acids and their esters with lower alkanols and lower alkanediols, unsaturated aliphatic hydrocarbon alcohols having from 8 to 18 carbon atoms and triglycerides of higher fatty acids including unsaturated higher fatty acids using performic acid formed in situ from hydrogen peroxide and formic acid in an aqueous media consisting essentially of passing the reactants, the unsaturated oily compound pound and the hydrogen peroxide/formic acid aqueous phase under ambient pressure in cross-counter flow through an at least three-stage reaction cascade from stage 1 to stage n, of which the individual stages each consist of a stirrer-equipped reaction vessel and a phase separator, the dily phase being introduced into the first reaction stage, the concentrated hydrogen peroxide solution being introduced into the penultimate reaction stage or being divided and a part introduced as a separate stream into one or more of the stages n−1 to 2 and the concentrated formic acid solution being introduced as a separate stream into one or more of the stages n−1, n−2 or n−3 to 2, the oily phase and the hydrogen peroxide/formic acid aqueous phase or acid water phase being separated from one another in a phase separator in each reaction stage after issuing from the reactor and the olefinic phase successively passing through reaction stages 1 to n, while the acid water phase, after reaction stage (n−1), passes successively through the reaction stages (n−2) to 2 in counter flow to the olefin phase and then successively through stages n and 1, while the reaction temperature is maintained between 50° and 80° C. in the reactors and between 15° and 60° C. in the phase separators, and continuously recovering an epoxidized oily compound from reaction stage n and an acid water phase from reaction stage 1.

2. The process of claim 1 wherein, in reaction stage n after separation of the acid water phase, the oily phase is passed into another stirrer-equipped reactor for the olefin-epoxide phase which is operated at a temperature in the range from 30° to 70° C. and in which the unseparated fractions of hydrogen peroxide and formic acid or performic acid which are dissolved or suspended in the olefin-epoxide phase are able to react with the as yet unreacted double bonds of the olefin.

3. The process of claim 1 wherein said concentrated formic acid solution is introduced as a separate stream in reaction stage n−1.

4. The process of claim 2 wherein said concentrated formic acid solution is introduced as a separate stream in reaction stage n−1.

5. The process of claim 1 wherein said concentrated formic acid solution is divided and introduced as a separate stream into more than one of the stages n−1 to 2.

6. The process of claim 2 wherein said concentrated formic acid solution is divided and introduced as a separate stream into more than one of the stages n−1 to 2.

7. The process of claim 5 wherein said concentrated formic acid solution is divided and introduced as a separate stream into stages n−2 and n−3.

8. The process of claim 6 wherein said concentrated formic acid solution is divided and introduced as a separate stream into stages n−2 and n−3.

9. The process of claim 1 wherein the phase separators of the reaction stages are operated with graduated cooling, the heavier acid water phase being cooled to between 15° and 40° C. and the lighter oily olefin/epoxide phase to a temperature of brom 30° to 60° C.

10. The process of claim 1 wherein said reaction temperature is maintained between 60° to 70° C. in the reactors.

11. The process of claim 9 wherein said reaction temperature is maintained between 60° to 70° C. in the reactors.

12. The process of claim 11 wherein said lighter oily olefin/epoxide phase is cooled to a temperature of from 40° to 50° C. in the phase separators.

13. The process of claim 1 wherein the position of the separating layer between the olefin/epoxide phase and the acid water phase in the separators is adjusted in such a way that the ratio by volume between the acid water phase and the oily olefin/epoxide phase in the separators is smaller than or at most equal to that of the input streams, so that the average residence time of the acid water phase in the separators is shorter than or at most equal to that of the oily olefin/epoxide phase 14. The process of claim 1 wherein said phase separators have an inert packing whereby convection currents are suppressed.

* * * * *